(12) United States Patent
Gross et al.

(10) Patent No.: US 12,016,871 B2
(45) Date of Patent: Jun. 25, 2024

(54) COMPOSITIONS FOR ORAL CANCER OR AN OROPHARYNGEAL CANCER

(71) Applicant: GR BIOSYSTEMS, INC., Draper, UT (US)

(72) Inventors: Andrew J. Gross, Draper, UT (US); Shane Ririe, Draper, UT (US)

(73) Assignee: GR BIOSYSTEMS, INC., Draper, UT (US)

(*) Notice: Subject to any disclaimer, the term of this patent is extended or adjusted under 35 U.S.C. 154(b) by 0 days.

(21) Appl. No.: 17/249,976

(22) Filed: Mar. 19, 2021

(65) Prior Publication Data

US 2021/0290647 A1 Sep. 23, 2021

Related U.S. Application Data

(60) Provisional application No. 62/992,350, filed on Mar. 20, 2020.

(51) Int. Cl.
| | |
|---|---|
| *A61K 31/7034* | (2006.01) |
| *A61K 9/00* | (2006.01) |
| *A61K 31/12* | (2006.01) |
| *A61K 31/121* | (2006.01) |
| *A61K 31/16* | (2006.01) |
| *A61K 31/4164* | (2006.01) |
| *A61K 31/43* | (2006.01) |
| *A61K 31/65* | (2006.01) |
| *A61K 31/7048* | (2006.01) |
| *A61K 31/7052* | (2006.01) |
| *A61K 31/7056* | (2006.01) |
| *A61K 47/34* | (2017.01) |
| *A61P 35/00* | (2006.01) |

(52) U.S. Cl.
CPC ........ *A61K 31/7034* (2013.01); *A61K 9/0014* (2013.01); *A61K 9/0053* (2013.01); *A61K 9/0063* (2013.01); *A61K 31/12* (2013.01); *A61K 31/121* (2013.01); *A61K 31/16* (2013.01); *A61K 31/4164* (2013.01); *A61K 31/43* (2013.01); *A61K 31/65* (2013.01); *A61K 31/7048* (2013.01); *A61K 31/7052* (2013.01); *A61K 31/7056* (2013.01); *A61K 47/34* (2013.01); *A61P 35/00* (2018.01)

(58) Field of Classification Search
CPC .. A61K 31/7034; A61K 31/12; A61K 31/121; A61K 31/16; A61K 31/4164; A61K 31/43; A61K 31/65; A61K 31/7048; A61K 31/7052; A61K 31/7056; A61K 47/34; A61K 9/0014; A61K 9/0053; A61K 9/006; A61K 9/0063; A61P 35/00
See application file for complete search history.

(56) References Cited

U.S. PATENT DOCUMENTS

2015/0313925 A1* 11/2015 Fiorentino ........... A61K 31/235
514/34

FOREIGN PATENT DOCUMENTS

KR 1020170026896 A * 3/2017 ......... A61K 31/7024

OTHER PUBLICATIONS

Zhang et al., Pharmaceutical Research, 2009, 26(9), p. 2066-2080. (Year: 2009).*
Pai, A., Journal of Medicine, Radiology, Pathology & Surgery, 2002, 453, p. 149-158. (Year: 2002).*
Lee et al., Archives of Oral Biology, 2008, 53, p. 801-809. (Year: 2008).*
Patnaik et al., Annals of Biomedical Engineering, 2019, 47(1), p. 39-59, published online Oct. 8, 2018. (Year: 2018).*
Zhang et al., Experimental Cell Research, 2019, 384, article 111634, 10 pages, Available online Sep. 18, 2019. (Year: 2019).*
Ho et al., European Journal of Pharmacology, 2002, 453, p. 149-158. (Year: 2002).*
Kuo et al., J. Agric. Food Chem., 2009, 57, p. 3331-3339. (Year: 2009).*
Hu et al., Mol. Cancer Ther., 2008, 7(9), p. 2681-2691. (Year: 2008).*

* cited by examiner

*Primary Examiner* — Jonathan S Lau
(74) *Attorney, Agent, or Firm* — Ryan L. Marshall; Barnes & Thornburg LLP

(57) ABSTRACT

The present disclosure generally relates to compositions that inhibit matrix metalloproteinases (MMPs). These compositions may be particularly useful in treating oral cancer or an oropharyngeal cancer. The compositions can be prepared as a topical formulation, ointment, mouthwash, or packaged in a syringe.

20 Claims, 4 Drawing Sheets

COMPOSITIONS FOR ORAL CANCER OR AN OROPHARYNGEAL CANCER

CROSS-REFERENCE OF RELATED APPLICATIONS

The present application claims the benefit of and priority to U.S. Provisional Application No. 62/992,350, filed Mar. 20, 2020, the contents of which are incorporated herein by reference in their entirety.

BACKGROUND

1. Field of the Invention

The present disclosure generally relates to compositions for inhibiting matrix metalloproteinases (MMPs). More particularly the disclosure relates to compositions including an MMP inhibitor for treating an oral cancer or an oropharyngeal cancer.

2. Description of the Related Art

Oral cancer is the 6th most common cancer worldwide with over 49,000 new cases expected in 2017 in the United States alone. Cancer of the oral cavity and oropharynx results in approximately 9700 deaths each year, with only a 50-60% 5-year survival rate. One reason for the poor outcomes associated with oral cancer is that a large percentage of cases are first diagnosed in an advanced stage. Tumor biology is an extremely complex process and oral carcinogenesis involves a series of concerted steps including pre-cancerous lesions, invasion, and metastasis. In addition to early diagnosis, research to develop new therapies targeted at tumor spread represent a potential strategy to lessen morbidity and mortality for those affected by oral squamous cell carcinoma (OSCC).

The concept of the tumor microenvironment (TME) has emerged as an integral aspect of carcinogenesis. The TME contains several cell types such as macrophages, T cells, and carcinoma-associated fibroblasts (CAF) that often coevolve with a tumor. These cells appear to provide many of the signals that trigger the pleiotropic properties of cancer cells. As the disease progresses, CAF, cancer cells and macrophages also secrete factors such as MMPs that contribute to tumor invasiveness.

MMPs are calcium-dependent zinc-containing endopeptidases that degrade extracellular matrix (ECM), initially discovered by Gross and Lapiere in 1962. Additionally, metalloproteinase activity is now linked to the control of immune responses. Post-translational modification of proteins and activation of signal transduction pathways that control cytokine biosynthesis allow the MMPs to direct systemic inflammation or barrier immunity. As it is evident from their substrates, MMPs have a vast proteolytic potential that include collagen types I-XVII, pro forms of inflammatory molecules such as tumor necrosis factor (TNF), interleukin 18 (IL-18), monocyte chemoattractant protein (MCP) and even other pro forms of MMPs. When present in excess, MMPs severely compromise tissue function and integrity.

Most MMPs present with four distinct functional domains: signal peptide, propeptide, catalytic domain and hemopexin-like domain. All of the MMPs contain a highly homologous catalytic domain and a propeptide. The propeptide interacts with the $Zn^{2+}$ ion located in the catalytic pocket through a cysteine residue and keeps the enzyme in a latent, inactive state. The propeptide must be removed to allow for enzyme activity through a pathway that varies according to the MMP subfamily.

New therapeutics approaches are needed that focus on changing the inflammatory process. Effective control of the immune response may slow down the disease progression, improve clinical outcomes and even prevent metastasis.

BRIEF SUMMARY

In some embodiments, a method of treating an oral cancer or an oropharyngeal cancer is provided. The method may include administering to a subject in need thereof a composition comprising 1,2,3,4,6-penta-O-galloyl-␤-D-glucose (PGG).

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DETAILED DESCRIPTION

Figure 1:
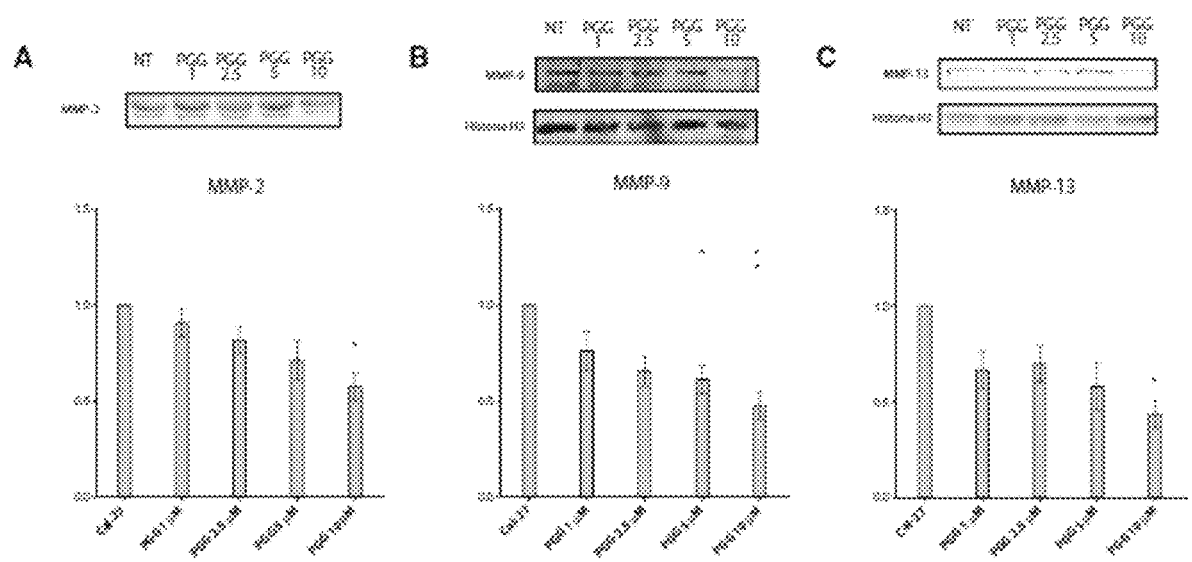
FIG. 1 shows that PGG prevents the upregulation of MMP-2, MMP-9 and MMP-13Cal-27 cells (squamous cell carcinoma) when treated with PGG at different concentrations for 48 hours. (A) MMP-2 expression was not significantly different to the non-treated group (NT) when cells were treated with 1, 2.5, or 5 μM PGG ($p>0.05$, $n=4$) (one-way ANOVA). MMP-2 expression was significantly decreased when Cal-27 cells were treated with 10 μM PGG ($p<0.01$, $n=4$) (one-way ANOVA, Bonferroni). Samples were obtained from cell media. (B) MMP-9 expression was not significantly different to the non-treated group (NT) when cells were treated with 1 or 2.5 μM PGG ($p>0.05$, $n=4$) (one-way ANOVA); MMP-9 expression was significantly decreased when Cal-27 cells were treated with 5 or 10 μM PGG ($p<0.05$ and $p<0.01$ respectively, $n=4$) (one-way ANOVA). Samples were obtained from cytoplasmic protein extraction and normalized to Histone H3. (C) MMP-13 expression was not significantly different to the nontreated group (NT) when cells were treated with 1, 2.5 or 5 μM PGG ($p>0.05$, $n=4$) (one-way ANOVA). MMP-13 expression was significantly decreased when Cal-27 cells were treated with 10 μM PGG ($p<0.01$, $n=4$) (one-way ANOVA, Bonferroni). Samples were obtained from cytoplasmic protein extraction and normalized to Histone H3.

Various embodiments are described below with reference to the drawings. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Despite having the largely preventable risk factors of tobacco and alcohol use, oral squamous cell cancer remains a serious, growing public health problem. Despite research seeking new treatment alternatives, survival rates have failed to significantly improve over the past decade. Even the presence of a single metastatic cervical lymph node drops OCSS survival rates by 50%, highlighting the potential benefit of therapy targeted at reducing tumor spread. The present disclosure relates to methods for treating oral or oropharyngeal cancer. The compositions may include poly galloyl glucopyranose.

Poly galloyl glucopyranose or 1,2,3,4,6-penta-O-galloyl-β-D-glucose (PGG, formula (I) shown below) is a polyphenolic gallotannin synthesized by plants. It was initially extracted from *Rhus typhina* (sumac) in 1990 by Hofmann and Gross.

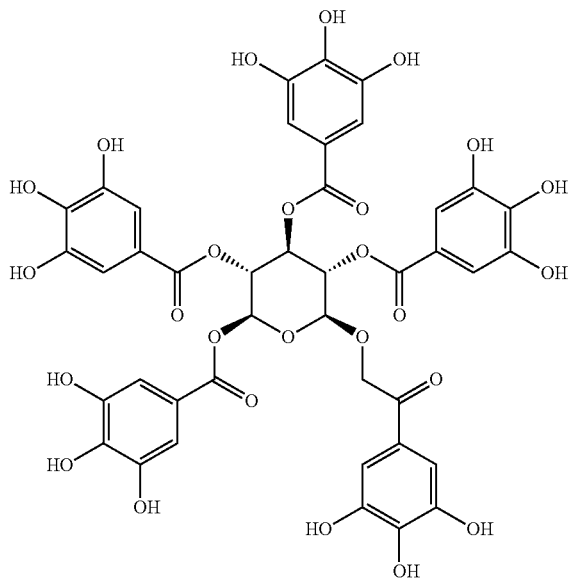 [SMILES: O=C(CO[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

PGG has been regarded as an inflammatory promoter for treatment of peripheral blood mononuclear cells (PBMCs) with PGG resulted in the production of TNF-α and IL-1β.

Posterior in vitro and in vivo studies in PBMCs demonstrated that PGG could attenuate the inflammatory effect of lipopolysaccharide (LPS), the major component of the cell wall of Gram-negative bacteria. Studies have shown that PGG largely suppressed LPS-induced TNF-α production by as much as 90% with doses as low as 5 μM. In peritoneal and colonic macrophages, PGG did not interfere with the binding of LPS to the toll-like receptors 4 (TLR4) but interacted directly with MyD88 adaptor protein thereby decreasing the production of TNF-α, IL-1β and IL-6.

In a prior disclosure, it was disclosed that PGG and other compounds act as an inhibitor for the protein and gene expression of MMPs, and MMP expression is clinically relevant to the progression of periodontitis. The U.S. patent application Ser. No. 16/496,559 is hereby incorporated by reference in its entirety.

For the purposes of this disclosure PGG may also refer to variants of the structure depicted above, for example variants or PGG-like molecules may include structures where the some or all the outer hydroxyl groups are replaced with a $C_1$-$C_8$ alkyl group, where the alkyl group may be methyl. Other PGG-like molecules may have several hydroxyl groups removed from the outer phenyl rings.

A method of treating an oral cancer or an oropharyngeal cancer is provided. The method may include administering to a subject in need thereof a composition comprising 1,2,3,4,6-penta-O-galloyl-β-D-glucose (PGG).

In some embodiments, the composition may include a pharmaceutically acceptable carrier and a compound selected from PGG, curcumin, deferoxamine, chloromethyl ketone, and combinations thereof.

In some embodiments, the compound is PGG. In some embodiments, the compound is curcumin. In some embodiments, the compound is deferoxamine. In some embodiments, the compound is chloromethyl ketone.

In some embodiments, the composition includes a mixture of two or more of PGG, deferoxamine, chloromethyl ketone, and curcumin. In some embodiments, the mixture is PGG and deferoxamine. In some embodiments, the mixture is PGG and chloromethyl ketone. In some embodiments, the mixture is PGG and curcumin. In some embodiments, the mixture is deferoxamine and chloromethyl ketone. In some embodiments, the mixture is deferoxamine and curcumin. In some embodiments, the mixture is chloromethyl ketone and curcumin.

In some embodiments, the mixture is PGG, deferoxamine, and chloromethyl ketone. In some embodiments, the mixture is PGG, deferoxamine, and curcumin. In some embodiments, the mixture is PGG, chloromethyl ketone, and curcumin. In some embodiments, the mixture is deferoxamine, chloromethyl ketone, and curcumin. In some embodiments, the mixture is PGG, deferoxamine, chloromethyl ketone, and curcumin.

In some embodiments, the composition may include from 0.00001% to 50% by volume of the active compound or compounds. The composition may include from 0.00001% to 30% by volume, 0.00001% to 20% by volume, or 0.00001% to 10% by volume of the compound. In some embodiments, the composition may include 0.001% to 30% by volume, 0.01% to 30% by volume, 0.1% to 30% by volume, or 1% to 30% by volume of the active compound or compounds.

In some embodiments, the pharmaceutically acceptable carrier is selected from poly(glycolide-co-dl-lactide)

(PGLA), polyethylene glycol, collagen, hyaluronic acid, liposome, micelle, dendrimer, and combinations thereof.

In some embodiments, the pharmaceutically acceptable carrier is PGLA. The PGLA polymer may be in the form of a microsphere. PGLA is a bioerodible polymer that can be prepared by ring-opening copolymerization of glycolide and lactide. Glycolide and lactide exist in two stereoisomeric forms: D and L. D,L lactide may be especially useful in producing copolymers for drug delivery applications. PGLA microspheres may be prepared by water/oil/water (W/O/W) and solid/oil/water (S/O/W) double emulsion solvent evaporation method or other methods such as nanoprecipitation, emulsion, solvent diffusion, or salting-out. The compounds of this disclosure may be incorporated into the matrix of a PGLA microsphere or contained within an aqueous core of the microsphere.

In some embodiments, the compounds may be encapsulated within a liposome or micelle. Encapsulation provides extended and controlled release of the compounds at the application site. Methods of preparing liposomes and micelles are commonly known in the art.

In some embodiments, the composition may also include an antibiotic, anti-inflammatory, analgesic agent, or any combination thereof. The anti-inflammatory may be a corticosteroid such as but not limited to hydrocortisone or triamcinolone acetonide. The analgesic agent may be lidocaine, articaine, mepivacaine, bupivacaine, salts thereof, or mixtures thereof. The analgesic agent may be co-administered with epinephrine. The antibiotic may be tetracycline, doxycycline, metronidazole, clindamycin, amoxicillin and clavulinic acid (augmentin), azithromycin, metronidazole, spiramycin, minocycline, or any combination thereof.

In some embodiments, the composition may include water, a buffer, or a flavoring. A buffer may be included to maintain a pH of the composition. The composition may have a pH ranging from about 4 to about 9.

In some embodiments, the subject may be a human or other mammal. In some embodiments, the subject is a human. In some embodiments, the subject is a canine. In some embodiments, the subject is a feline. In some embodiments, the subject may be a horse. The compositions may be administered orally or topically.

In some embodiments, the composition may be in the form of a mouthwash. In some embodiments, the composition may be in the form of an ointment, gel, foam, or spray.

In some embodiments, the composition may be administered sub-gingivally. The composition may contact human gingival fibroblasts or mucosal fibroblasts. In some embodiments, the composition may be loaded into a syringe. The syringe may comprise a needle that can be applied to the region of the oral cavity that is diseased.

The method may include administering to a subject a topical composition. The composition may be any composition described above.

In some embodiments, the composition may be in the form of a patch. The patch may be applied to the inside the mouth. The patch may include an adhesive so that once it is applied the patch can remain at the treated site.

In some embodiments, the composition may contact keratinized, parakaratinized, non-keratinized epithelium and combinations of the same.

In some embodiments, the subject has an oropharyngeal cancer.

The oropharyngeal cancer may be HPV-positive oropharyngeal cancer or an oropharyngeal cancer linked to alcohol or tobacco use.

In some embodiments, the subject has an oral cancer.

The oral cancer may be squamous cell carcinoma, verrucous carcinoma, minor salivary gland carcinoma, lymphoma, or a benign oral cavity tumor. In some embodiments, the oral cancer may be squamous cell carcinoma.

In some embodiments, the oropharyngeal cancer or oral cancer is metastatic.

EXAMPLES

Example 1

Squamous cell carcinoma cells (Cal 27) were purchased from ATCC (CRL-2095) and grown in DMEM with Glutamax, 10% FBS and Penicillin/Streptomycin (1055-024, 15140-122, 10438-018 Gibco-ThermoFischer Scientific) and kept at 37° C. in a humidified air chamber with 5% $CO_2$. Cells were seeded at $3 \times 10^5$ cells/flask for the experiments and then grown to confluency. Cells between 3 and 10 passages were used for all experiments.

1,2,3,4,6-Penta-O-galloyl-β-D-glucose (G7548, Sigma-Aldrich) was dissolved in dimethylsulfoxide (DMSO) to obtain a 100 mM stock solution. Subsequent dilutions were done using water, and no flask contained more than 0.5 μL of DMSO (0.01%). Cells were simultaneously induced with PGG at concentrations of 1 μM, 2.5 μM, 5 μM or 10 μM according to results FIGS. 1, 2, 3, 4, and then incubated for 48 hours.

During the protein extraction, media were collected, flash frozen and saved for BCA, Western Blot, and ELISA analysis. Cells were washed with cold PBS and lysed with RIPA buffer (150 mM NaCl, 50 mM Tris, 1% Sodium deoxycholate, 1% Triton X-100 and 0.1% SDS) and collected with a cell scraper and centrifuged at 14,000 rpm for 30 min. The supernatant was collected and assayed for protein concentration using a BCA Assay.

Samples were mixed with 4×SDS Loading buffer (40% Glycerol, 8% SDS, 200 mM Tris-HCl, 400 mM Dithiothreitol, 0.005% bromophenol blue), heated to 95° C., and then frozen for further analysis.

12% Sodium dodecyl sulfate (SDS)—polyacrylamide gels were prepared by standard methods, loading 30 μg of protein per lane and electrophoresed for 1 hour at 150 V.

Proteins from gels transferred to 0.45 μm nitrocellulose paper were then blocked with odyssey blocking buffer. Primary antibodies were diluted in blocking solution containing 0.1% Tween and incubated overnight at 4° C. with monoclonal antibodies to MMP-1, MMP-3, MMP-2, MMP-9, Stat3, pStat3, MMP-8 and MMP-13, and MMP-14. Blots were normalized by probing the membranes with Histone H3.

Secondary antibody incubation was performed in a blocking solution of 0.2% Tween with IRDye 800CW Goat anti-Rabbit IgG and IRDye® 680RD Donkey anti-Mouse IgG. The proteins were detected and visualized by fluorescence using the LI-COR Odyssey Classic Infrared Imaging system (LI-COR Biosciences). Densitometry analysis of specific bands was performed with the Image Studio software provided by LI-COR Biosciences and the images analyzed using ImageStudio (LI-COR Biosciences). Statistical analysis, including one-way ANOVA with Dunnett's Multiple Comparison Test and Bonferroni, was done using GraphPad Prism 7 (Graph-Pad Software, La Jolla, CA, USA). p values were calculated using the unpaired two-sided Student's t test to compare groups, with statistical significance set at $p<0.05$.

After washing the tissue culture with 1× phosphate buffered saline (PBS), the cells were lysed, and the RNA purified using a Qiagen RNeasy mini kit using the manufacturer's recommended protocol. All samples were treated with Qiagen DNase. One microgram of RNA was used for reverse transcription and subsequent SYBR® Green real time PCR for the genes of interest as previously described. Reverse transcription kits (Cat #330401) and SYBR Green real-time PCR master mixes were from Qiagen.

The following primers and probes were used: Human MMP-2; MMP2, Human MMP-9; MMP9, Human MMP-13; MMP13, Human MMP-14; MMP14, and Human glyceraldehyde 3-phosphate dehydrogenase; GAPDH.

Real time quantitative PCR was performed using an Applied Biosciences StepOne plus instrument and analyzed with StepOne software v2.3. The relative amounts of transcripts from each gene were normalized to reference gene GAPDH and calculated as follows: $\Delta\Delta CT$=the average $\Delta CT$ of sample B–the average $\Delta CT$ of sample B, and their fold difference=$2-\Delta\Delta CT$.

Transmembrane/Boyden assay plates with Matrigel were purchased from Corning. DMEM with 10% FBS was used as a chemoattractant in the lower chamber while the cells in the upper chamber were cultured in DMEM with 1% FBS. Wells were prepared with different concentrations of PGG (0-10 µM) and left to incubate for 24 hour. After 24 hour media has discarded and the cells invading the Matrigel were counted according to established protocols.

In the Cal 27 cell line, MMP-2 was released into the paracellular space and activated by MMP-14. Subsequently, MMP-2 and MMP-14 activate MMP-13. MMP-9 requires different molecules for activation. After incubating Cal-27 cells with PGG at different concentrations (1, 2.5, 5 and 10 µM), Cal-27 cells showed a dose-dependent decline of MMP-2 and MMP-13 release and at the 10 µM concentration the secretion was significantly lower than the non-treated cell group (FIG. 1A, 1C) MMP-9 secretion also decreased in a dose-dependent manner, becoming significantly lower than the non-treated group when PGG concentration reached 5 µM (FIG. 1B).

Figure 2:
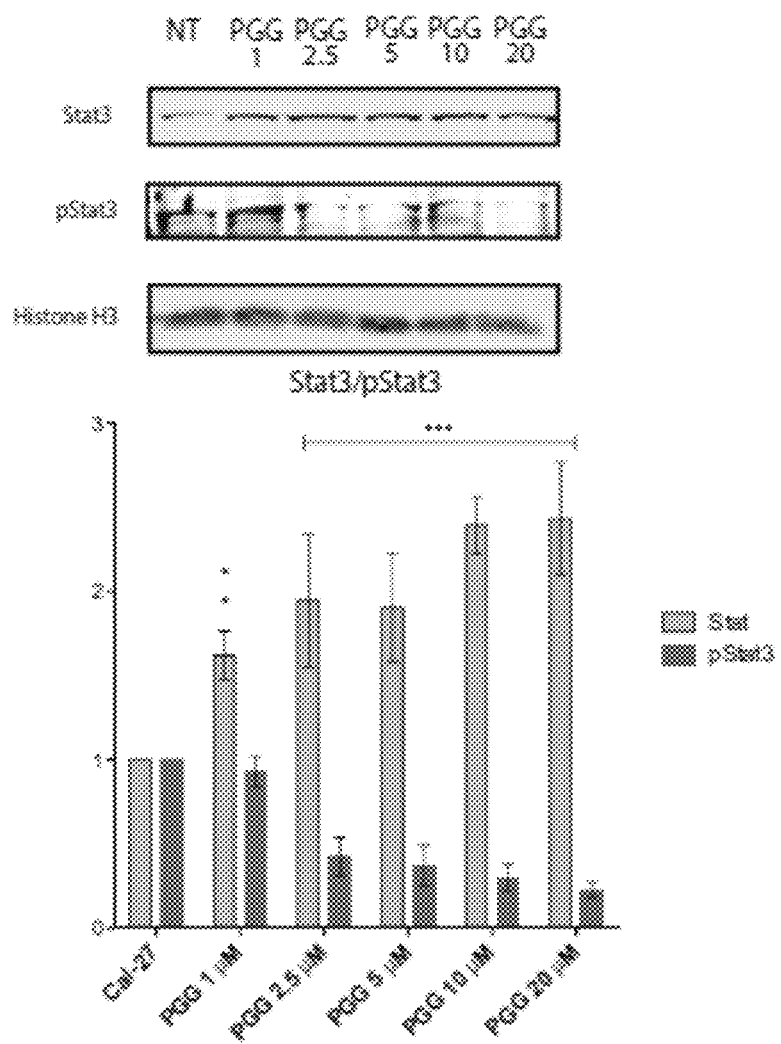
FIG. 2 shows PGG decreases Stat3 phosphorylation production in Cal-27 cells (squamous cell carcinoma) when treated with PGG at different concentrations for 48 hours. PGG treatment significantly decreases Stat3 phosphorylation (pStat3) ($p<0.0001$, $n=4$) (two-way ANOVA). Non-phosphorylated Stat3 was significantly higher than Stat3 in non-treated Cal-27 cells ($p<0.0001$, $n=4$) (two-way ANOVA). Samples were obtained from cytoplasmic protein extraction and normalized to Histone H3.

PGG decreases phosphorylation of Stat3. Our results demonstrated a decrease of Stat3 phosphorylation in the presence of varying concentrations of the small molecule PGG (FIG. 2). Results revealed an increase in total Stat3 when the cells were treated with PGG at varying concentrations. Despite a higher concentration of Stat3 present as substrate for phosphorylation to pStat3, PGG prevented the activation of this proinflammatory signal transducer.

Figure 3:
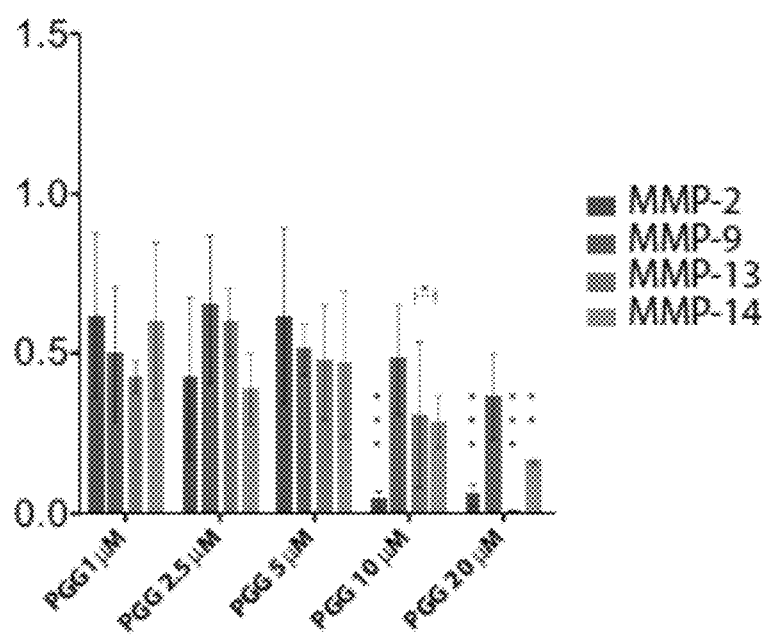
FIG. 3 shows mRNA expression of MMPs after treatment of Cal-27 cells with PGG. Graph shows expression of MMP-2, MMP-9, MMP-13 and MMP-14 genes after PGG treatment (1, 2.5, 5, 10 and 20 μM). MMP-2 gene expression is significantly decreased with PGG at 5 and 10 μM ($p<0.0001$, twoway ANOVA) ($n=4$). MMP-9 expression was not significantly different to the non-treated group (NT) at any PGG dose (p>0.05, n=4) (two-way ANOVA, Bonferroni). MMP-13 expression is decreased when Cal-27 cells are treated with 10 or 20 μM PGG (p<0.05 and p<0.001, respectively, two-way ANOVA). MMP-13 gene expression is decreased when Cal-27 cells are treated with 10 or 20 μM PGG (p<0.05 and p<0.001, respectively, two-way ANOVA) (p<0.0001, two-way ANOVA) (n=4). Housekeeping gene used was GAPDH.

PGG decreased the expression of MMP-2, MMP-13, and MMP-14 in a dose-dependent manner. These data revealed that treatment with PGG at 10-20 µM reduces MMP-2, MMP-13, and MMP-14 expression when compared with non-treated Cal-27 (FIG. 3). MMP-9 gene expression did not significantly decrease with PGG, despite a decrease in the protein secretion with concentrations of PGG 5 µM and higher.

Figure 4:
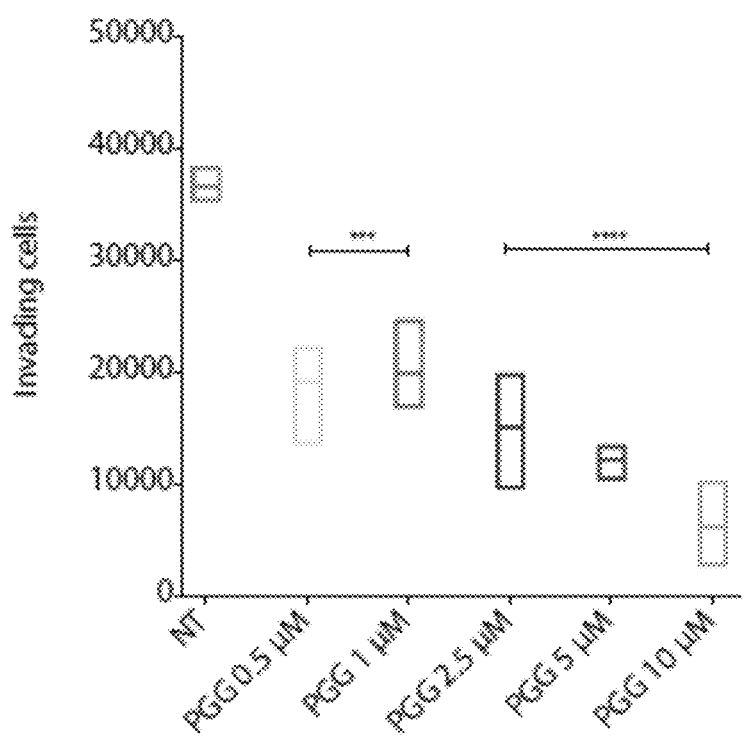
FIG. 4 shows that PGG decreases invasiveness of Cal 27 cells. The graph shows number of cells invading through Matrigel in the transmembrane/Boyden cell chamber. Number of cells invading through Matrigel was significantly lower in wells treated with PGG at 0.5 and 1 μM (p<0.001, n=4) (one-way ANOVA) and 2.5, 5 and 10 μM p<0.0001, n=4) (one-way ANOVA).

PGG reduces invasion of Cal 27 cells in a Matrigel transwell assay. FIG. 4 illustrates the effects of PGG on the invasion of Cal 27 cells in vitro using Matrigel-coated transwells assay (FIG. 4). The data showed a significant decline in the percentage of cells invading the membrane after 24 hour treatment when compared with the untreated control. The inhibitory effect is evident even with 0.5 µM PGG, with a maximum effect at 10 µM PGG (44.5% and 22.3%, respectively, FIG. 4).

Despite having the largely preventable risk factors of tobacco and alcohol use, oral squamous cell cancer remains a serious, growing public health problem. Despite research seeking new treatment alternatives, survival rates have failed to significantly improve over the past decade. Even the presence of a single metastatic cervical lymph node drops OCSS survival rates by 50%, highlighting the potential benefit of therapy targeted at reducing tumor spread.

These findings showed that the small molecule inhibitor PGG can decrease MMP secretion and invasiveness in vitro through a Stat3 mechanism in Cal 27 cells. These results indicate that Cal 27 cells constitutively secrete MMP-2, -9, and -13. More importantly, they demonstrate that PGG inhibits the production of these MMPs in a dose-dependent manner. The Stat3/pStat3 effect is further reflected by decreases in MMP gene expression, accounting at least partly for the protein expression data for MMP-2, -9, and -13.

This study indicates that PPG is a small molecule that reduces the expression of matrix metalloproteinases and inhibits the metastatic spread of the Cal-27 squamous cell carcinoma cell line. By controlling the expression of molecules responsible for metastasis, PPG may offer a new therapeutic option for treating oral squamous cell carcinoma or other oral and oropharyngeal cancers.

All of the compositions, materials, and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is, therefore, intended that such changes and modifications be covered by the appended claims.

What is claimed is:

1. A method of treating an oral cancer or an oropharyngeal cancer, comprising:
    administering to a subject in need thereof a composition comprising a therapeutically effective amount of 1,2,3,4,6-penta-O-galloyl-β-D-glucose (PGG) and a pharmaceutically acceptable carrier, and
    reducing the expression of a matrix metalloproteinase selected from the group consisting of MMP-2, MMP-13, MMP-14, and any combination thereof.

2. The method of claim 1, wherein the composition further comprises one or more of deferoxamine, chloromethyl ketone, and curcumin.

3. The method of claim 1, wherein the composition comprises from 0.00001% to 30% by volume of PGG.

4. The method of claim 1, wherein the pharmaceutically acceptable carrier is selected from the group consisting of poly(glycolide-co-dl-lactide) (PGLA), polyethylene glycol, collagen, hyaluronic acid, liposome, micelle, dendrimer, and any combination thereof.

5. The method of claim 1, wherein the pharmaceutically acceptable carrier is PGLA.

6. The method of claim 1, wherein the composition further comprises an antibiotic, anti-inflammatory agent, analgesic agent, or any combination thereof.

7. The method of claim 1, wherein the composition further comprises an antibiotic selected from the group consisting of tetracycline, doxycycline, metronidazole, clindamycin, amoxicillin, clavulinic acid, azithromycin, metronidazole, spiramycin, minocycline, and any combination thereof.

8. The method of claim 1, wherein the composition is administered orally.

9. The method of claim 1, wherein the composition is administered sub-gingivally.

10. The method of claim 1, wherein the subject is a human.

11. The method of claim 1, wherein administering comprises contacting keratinized, parakaratinized, or non-keratinized epithelium with the composition.

12. The method of claim 1, wherein the composition is administered in the form of an ointment, mouthwash, or patch.

13. The method of claim 1, wherein the subject has an oropharyngeal cancer.

14. The method of claim 13, wherein the oropharyngeal cancer is HPV-positive oropharyngeal cancer or an oropharyngeal cancer linked to alcohol or tobacco use.

15. The method of claim 1, wherein the subject has an oral cancer.

16. The method of claim 15, wherein the oral cancer is squamous cell carcinoma, verrucous carcinoma, minor salivary gland carcinoma, lymphoma, or a benign oral cavity tumor.

17. The method of claim 13, wherein the oropharyngeal cancer is metastatic.

18. The method of claim 15, wherein the oral cancer is metastatic.

19. A method of treating an oral cancer or an oropharyngeal cancer, comprising
administering to a subject in need thereof a composition consisting essentially of 1,2,3,4,6-penta-O-galloyl-β-D-glucose (PGG) for inhibiting matrix metalloproteinase activity and expression, and a pharmaceutically acceptable carrier,
wherein the matrix metalloproteinase is selected from the group consisting of MMP-2, MMP-13, MMP-14, and any combination thereof.

20. A method of treating an oral cancer or an oropharyngeal cancer, comprising
administering to a subject in need thereof a composition consisting of 1,2,3,4,6-penta-O-galloyl-β-D-glucose (PGG) for inhibiting matrix metalloproteinase activity and expression, and a pharmaceutically acceptable carrier,
wherein the matrix metalloproteinase is selected from the group consisting of MMP-2, MMP-13, MMP-14, and any combination thereof.

* * * * *